(12) United States Patent
Ceriani et al.

(10) Patent No.: US 11,524,311 B2
(45) Date of Patent: Dec. 13, 2022

(54) SPRAY DISPENSER

(71) Applicant: Polichem S.A., Val Fleuri (LU)

(72) Inventors: Daniela Ceriani, Besano (IT); Alexander Keller, Rottenbuch (DE)

(73) Assignee: Polichem S.A., Val Fleuri (LU)

( * ) Notice: Subject to any disclaimer, the term of this patent is extended or adjusted under 35 U.S.C. 154(b) by 55 days.

(21) Appl. No.: 16/304,717

(22) PCT Filed: Jun. 30, 2017

(86) PCT No.: PCT/EP2017/066368
§ 371 (c)(1),
(2) Date: Nov. 27, 2018

(87) PCT Pub. No.: WO2018/002354
PCT Pub. Date: Jan. 4, 2018

(65) Prior Publication Data
US 2019/0337002 A1 Nov. 7, 2019

(30) Foreign Application Priority Data
Jul. 1, 2016 (IT) .................. 102016000068649

(51) Int. Cl.
*B05B 12/36* (2018.01)
*B05B 1/28* (2006.01)
(52) U.S. Cl.
CPC .............. *B05B 12/36* (2018.02); *B05B 1/28* (2013.01)
(58) Field of Classification Search
CPC ..... B05B 12/16; B05B 12/3236; B05B 14/00; B05B 14/30; B05B 11/0005; B05B 1/14; B05B 1/28; B05B 12/32–36; B05B 7/005; B05B 7/0087; B65D 83/30; A61M 11/007
(Continued)

(56) References Cited

U.S. PATENT DOCUMENTS 4,087,022 A   5/1978   Zanetti-Streccia
4,158,361 A   6/1979   Kotuby
(Continued)

FOREIGN PATENT DOCUMENTS

CN   103463717 A   12/2013
JP   H08-57053 A    3/1996
(Continued)

*Primary Examiner* — Cody J Lieuwen
(74) *Attorney, Agent, or Firm* — Vos-IP, LLC

(57) ABSTRACT

The invention relates to a dispenser 20 for the spray delivery of a preparation 18. The dispenser comprises: a reservoir 22 suitable for containing the preparation 18, a mechanical pump 24, a load chamber 26, a nozzle 28 having a delivery axis, and a delivery cone 30 having an axis. The mechanical pump is able, whenever operated: to take a predetermined amount of preparation from the reservoir, to supply said amount of preparation to the load chamber upstream of the nozzle, and to create a delivery pressure in the load chamber. The nozzle is able to deliver said amount of preparation in the form of an aerosol spray 180. The dispenser according to the invention is characterized in that the delivery cone comprises, in the proximity of the nozzle, at least one through-hole 320 suitable for putting the inside of the delivery cone into communication with the surrounding environment.

14 Claims, 4 Drawing Sheets

(58) Field of Classification Search
USPC .................................................. 239/288, 103
See application file for complete search history.

(56) References Cited

U.S. PATENT DOCUMENTS

| | | | | |
|---|---|---|---|---|
| 5,520,735 | A * | 5/1996 | Mulder | ................... B05B 5/032 |
| | | | | 118/308 |
| 5,921,444 | A * | 7/1999 | Fuchs | ................... A61F 9/0008 |
| | | | | 222/321.9 |
| 6,113,008 | A | 9/2000 | Arsenault et al. | |
| 6,978,945 | B2 | 12/2005 | Wong et al. | |
| 2005/0279864 | A1 * | 12/2005 | Fan | ........................ B05B 12/36 |
| | | | | 239/525 |
| 2012/0318891 | A1 * | 12/2012 | Chou | ................... B05B 7/0087 |
| | | | | 239/291 |

FOREIGN PATENT DOCUMENTS

| | | | | |
|---|---|---|---|---|
| JP | 09253539 A | * | 9/1997 | ............. B05B 12/36 |
| JP | H11-099202 A | | 4/1999 | |
| WO | WO/2005/075015 A1 | | 8/2005 | |
| WO | WO/2010/133167 A1 | | 11/2010 | |
| WO | WO/2015/021954 A1 | | 2/2015 | |

* cited by examiner

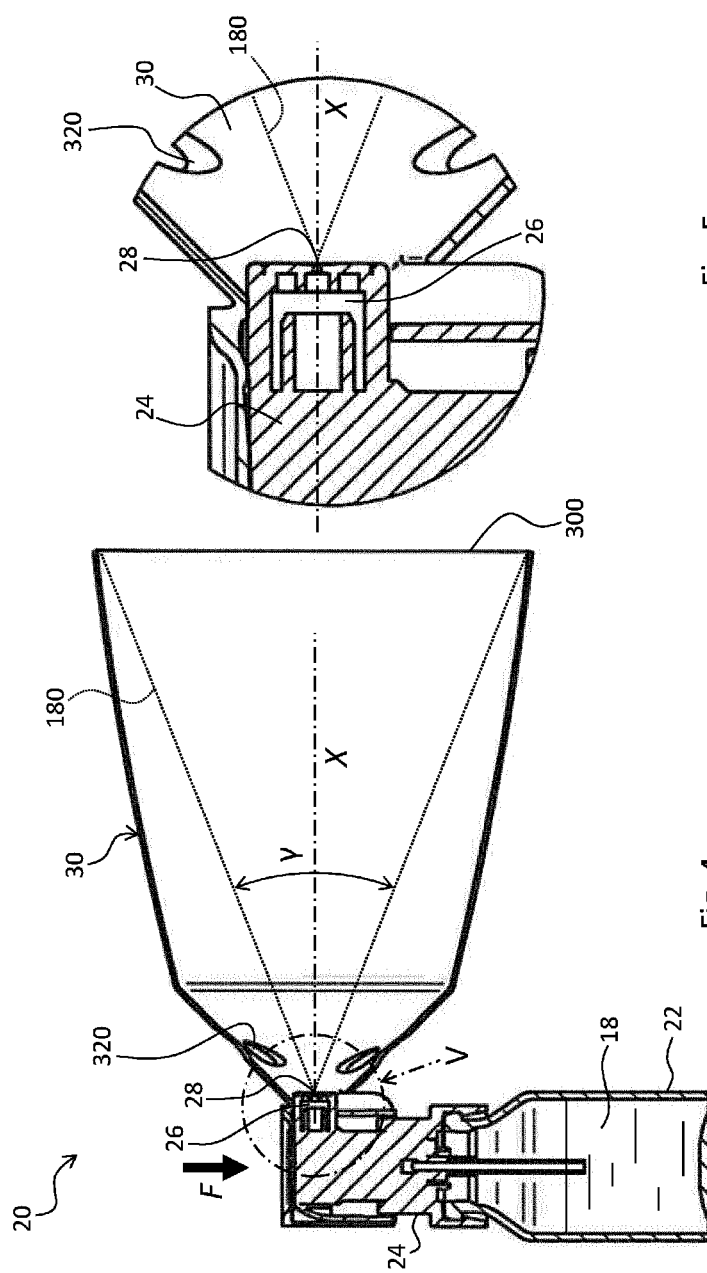

SPRAY DISPENSER

The present invention relates to a spray dispenser, and more particularly it relates to a spray dispenser for administering a preparation for therapeutic use, cosmetic use or similar. There are various types of spray dispensers, usually intended for delivering a liquid preparation in the form of aerosol, i.e. creating a spray of small droplets that form a spray plume.

Spray dispensers usually comprise a reservoir, which contains the preparation to be delivered, and a nozzle that is suitable for producing the aerosol plume.

Some dispensers use a propellant gas, contained in the reservoir together with the preparation to be delivered. Release of the pressurized gas entrains the preparation, forming the desired aerosol spray. There are, however, some disadvantages with using propellant gas, due to the possibility that the gas itself may react inside the reservoir with the preparation to be delivered or, more often, that once released into the environment it may react with the gases of the atmosphere.

Therefore other types of spray dispensers are used, of the mechanical type, which do not use a propellant gas. In this type of dispenser there is a load chamber immediately upstream of the nozzle. The mechanical action applied by the user on the dispenser fills the load chamber with preparation to be delivered and increases the pressure of the latter to about 2-4 bar. The overpressure within the load chamber causes sudden exit of the preparation through the nozzle, with consequent creation of the aerosol spray in the form of a spray plume.

Spray dispensers are commonly used in the pharmaceutical and cosmetic field, for administering a preparation containing a drug, an active principle, a medicinal product, a cosmetic or similar. In such cases, however, spray delivery may have some disadvantages.

Firstly, in the peripheral zones of the spray there is formation of a halo of extremely fine droplets that give rise to so-called fine mist and are easily dispersed in the surrounding environment. Dispersion of the fine mist is to be avoided for various reasons. Firstly, the fine mist carries with it a portion of the active principle to be administered, which is then deducted from the quantity actually administered. Moreover, the active principle thus dispersed is potentially dangerous for anyone not requiring the specific therapy. This danger must be avoided in particular for certain categories of subjects, such as, for example, women in pregnancy, neonates, babies and children of prepuberal age. Finally, the possible inhalation of the fine mist, which may contain a polymer, might lead to inflammatory reactions in the airways, including granulomas from foreign bodies.

Spray delivery often has the aim of dispersing the active principle on a patient's skin. In that case it is almost always necessary to be able to control the precise amount of preparation supplied per unit area, so as to avoid both an overdose, which is potentially dangerous, and administration of an insufficient and therefore ineffective amount.

As a person skilled in the art will understand, it can be assumed to a first approximation that the spray assumes a conical shape whose vertex coincides with the nozzle of the dispenser. Based on this observation, it will be understood that the amount of preparation supplied per unit area will depend on the distance of the nozzle from the patient's skin. In particular, the amount of preparation per unit area decreases at the rate of the square of the distance from the nozzle. For this reason, even a relatively small difference in the delivery distance leads to a large difference in the amount of preparation supplied per unit area.

In order to overcome the drawbacks mentioned above, improved spray dispensers have been proposed, comprising a delivery cone.

U.S. Pat. No. 6,978,945 describes a spray dispenser that has been improved in this sense. In this solution the delivery cone makes it possible on the one hand to avoid dispersion of the fine mist and on the other hand to control the delivery distance precisely. However, this solution is not fault-free. First of all, the delivery cone is not integral with the nozzle, which during delivery moves transversely relative to the axis of the cone. Moreover, this dispenser is constructed in a single piece which, once the preparation to be delivered has been exhausted, can no longer be re-used and must be disposed of. Finally, it is known that spray delivery within the closed system formed by the cone and the patient's skin does not guarantee the necessary uniformity of administration of the preparation. In fact, the air displaced during delivery of the preparation by the nozzle creates turbulence in the flow of the spray plume from the nozzle to the skin. This turbulence causes coalescence of portions of aerosol to form droplets of larger size than intended. Moreover, owing to the turbulence, it is possible that the spray may no longer assume the intended conical shape, resulting in impact of a portion of the preparation supplied on the inside walls of the delivery cone.

U.S. Pat. No. 6,113,008 describes another spray dispenser comprising a delivery cone. Not even this solution is fault-free. First of all the mechanical action required for delivery must be applied in the same direction as the axis of the delivery cone, a configuration that makes this dispenser rather inconvenient in some applications. Moreover, the delivery cone described here comprises ventilation slits positioned near the contact rim of the cone, i.e. where the latter rests on the user's skin. The position of these slits means that the aerosol spray generated by the nozzle is propagated in an almost closed environment, with consequences broadly similar to those already described for document U.S. Pat. No. 6,978,945. The ventilation slits have the dual purpose of balancing the pressure during delivery and of allowing the gaseous components of the preparation supplied to be dispersed in the environment. Document U.S. Pat. No. 6,113,008 makes explicit reference to the need to disperse any propellants, solvents, or similar in the environment, but it is obvious that these slits also allow unwanted dispersion of the fine mist.

The aim of the present invention is therefore to overcome at least partially the drawbacks mentioned above with reference to the prior art.

In particular, one aim of the present invention is to make available a spray dispenser that allows precise control of the amount of preparation supplied.

More particularly, one aim of the present invention is to make available a spray dispenser that makes it possible to avoid dispersion of the fine mist. A further aim of the present invention is to make available a spray dispenser that makes it possible to maintain the desired uniformity of administration of the preparation to be delivered.

The purpose and the aims stated above are achieved with a dispenser according to claim 1.

The features and further advantages of the invention will become clear from the description, given hereunder, of some embodiment examples, given for illustration, and non-limiting, referring to the appended drawings.

FIG. 4 shows a median section of the dispenser of FIG. 1;

FIG. 5 shows an enlarged view of the detail indicated with V in FIG. 4; and

Figure 1:
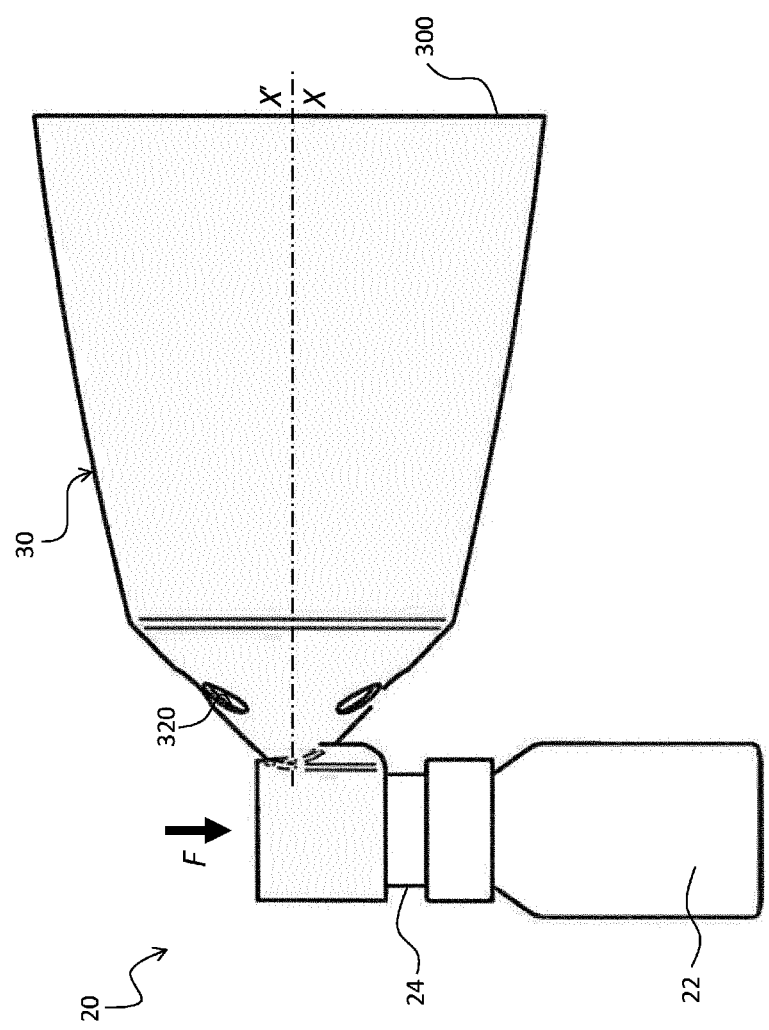
FIG. 1 shows a general side view of a dispenser according to the invention.
Figure 3:
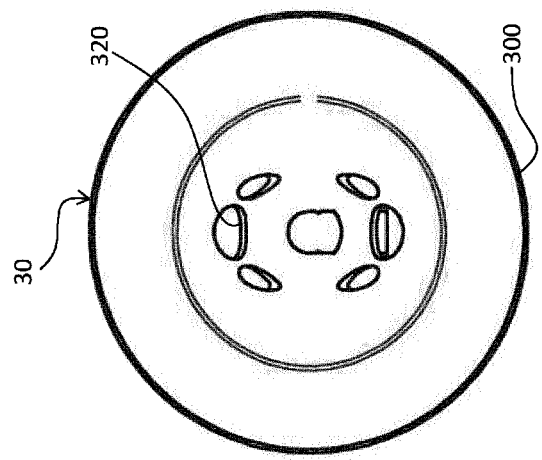
FIG. 3 shows a front view of the delivery cone of FIG. 2.
Figure 2:
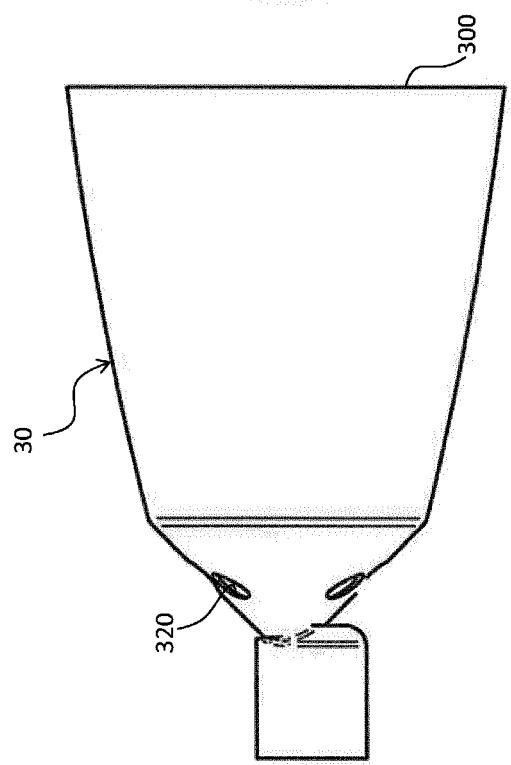
FIG. 2 shows a side view of the delivery cone of the dispenser of FIG. 1.

Referring to the appended figures, 20 indicates the whole of a dispenser for spray delivery of a preparation 18. The dispenser 20 according to the invention comprises:

a reservoir 22 suitable for containing the preparation 18,
a mechanical pump 24,
a load chamber 26,
a nozzle 28 having an axis; and
a delivery cone 30 having an axis.

The mechanical pump 24 is able, at each actuation:

to take a predetermined amount of preparation 18 from the reservoir 22,
to supply said amount of preparation 18 to the load chamber 26 upstream of the nozzle 28, and
to create a delivery pressure in the load chamber 26.

The nozzle 28 is able to deliver said amount of preparation 18 in the form of aerosol spray 180.

The dispenser 20 according to the invention is characterized in that the delivery cone 30 comprises, in the proximity of the nozzle 28, at least one through-hole 320 suitable for putting into communication the inside of the delivery cone 30 with the surrounding environment.

The dispenser according to the invention is mainly intended for a preparation 18 in liquid form, comprising an active principle intended for administration on a patient's skin. However, as a person skilled in the art will readily understand, the dispenser 20 may in the same way deliver any liquid substance, whether in the form of solution or suspension or emulsion, intended for treatment for therapeutic and/or cosmetic purposes.

As described, the at least one through hole 320 is suitable for putting into communication the inside of the delivery cone 30 with the surrounding environment. This means that the through hole 320 may be configured to form a fluidic connection through the delivery cone 30 between the inside of the delivery cone 30 and the surrounding environment. In other words, fluid can flow though the through hole 320 in the delivery cone 30 from the surrounding environment to inside the delivery cone 30 and vice versa.

As may be noted in particular in the appended FIGS. 1 and 4, the dispenser 20 according to the invention is activated by application of a force (indicated with F) by the user. The force F operates the mechanical pump 24 and therefore the dispenser 20 as a whole. As may be noted in the embodiment in the figures, the direction in which the force F is applied is substantially perpendicular to the direction of delivery of the preparation, said direction being defined by the delivery axis of the nozzle 28 and by the axis of the delivery cone 30 itself. The mechanical pump 24 may move the preparation by any mechanical action. Preferably, in the dispenser 20 according to the invention, the delivery axis of the nozzle and the axis of the delivery cone coincide in the single axis X, even during operation of the dispenser 20. Preferably, the axis X' of the delivery cone 30 is substantially through the centre of the delivery cone 30 along the length of the delivery cone 30. Preferably, the nozzle 28 is configured to provide the aerosol spray 180 along the delivery axis X, and the delivery axis X may be substantially through the centre of the aerosol spray 180.

Preferably, the delivery cone 30 comprises a contact rim 300 intended to rest on the patient's skin, so as to define and delimit the treatment area onto which the preparation will be delivered. Some dimensional relations will be exemplified hereunder in relation to the distance l between the nozzle 28 and the contact rim 300 measured along the axis X.

As already mentioned above, the at least one through-hole 320 is positioned in the proximity of the nozzle 28. According to the embodiments shown in the appended figures, at least one through-hole 320 is positioned within 20% of the distance l. For the avoidance of doubt, as the through hole is in the proximity of the nozzle, the 20% of the distance l between the nozzle 28 and the contact rim 300 is 20% of the distance l from the nozzle.

According to the embodiments presented in the figures, the delivery cone 30 comprises a plurality of through-holes 320. The through-holes 320 are preferably confined to a relatively narrow band of the surface of the cone 30. The band with the through-holes 320 may for example extend to about 10% of the distance l. Moreover, the through-holes 320 are preferably distributed according to criteria of symmetry.

Advantageously, the delivery cone 30 comprises two portions, indicated with 302 and 304 respectively, with different taper ratios. In particular, in the first portion 302 the generatrices form with axis X an angle $\alpha$ and in the second portion the generatrices form with axis X an angle $\beta$. Advantageously angle $\beta$ is smaller than $\alpha$.

Figure 6:
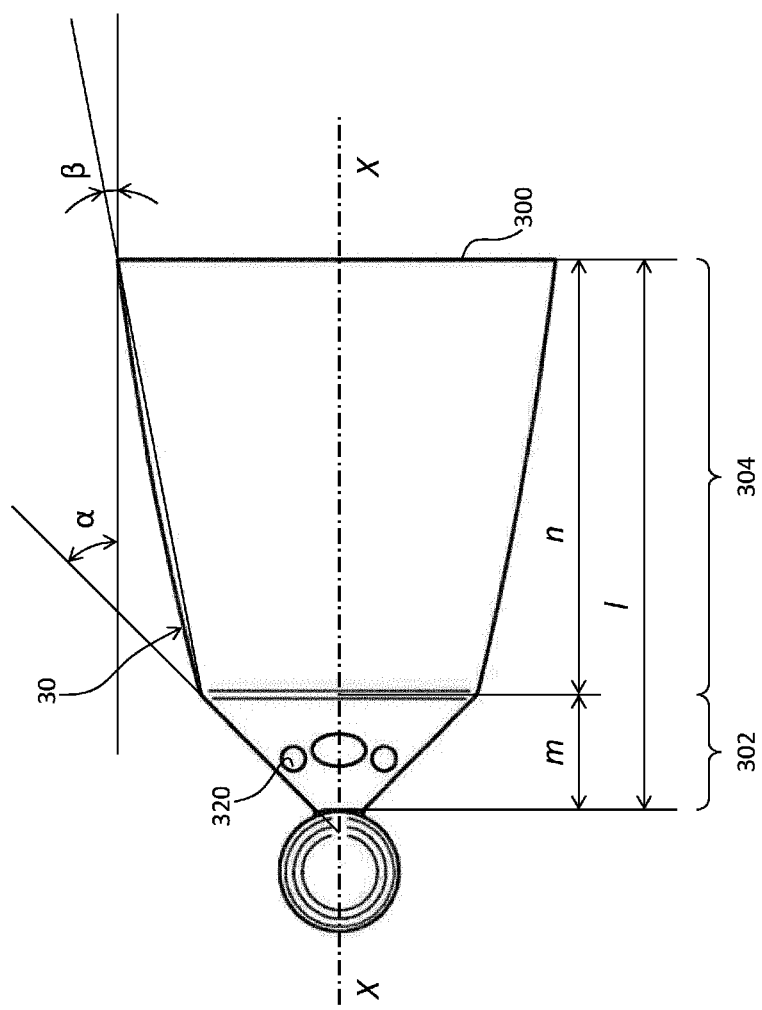
FIG. 6 shows a plan view of the delivery cone of FIG. 2.

In FIG. 6, for example, a specific embodiment is analysed from the geometric viewpoint. According to this embodiment, in the first portion 302 the generatrices of the cone form with axis X an angle $\alpha$ between 40° and 50°, preferably between 43° and 47°. Additionally or alternatively, in the second portion 304 the generatrices of the cone form with axis X an angle $\beta$ of between 6° and 16°, preferably between 9° and 13°.

Specifically in FIG. 6, it can be seen that the second portion is slightly convex, therefore its generatrix is not a segment of a straight line but a line with a very slight curvature. For the purposes of the invention, however, this detail is not at all relevant, and approximation of the generatrix with a segment of a straight line is broadly acceptable.

As a person skilled in the art can see from FIG. 6, in this embodiment the first portion 302 can extend to about 15%-25% of the distance l (section m in FIG. 6). The rest of the development of the cone is occupied by the second portion 304 with lower taper ratio (section n in FIG. 6).

According to the embodiment in the appended figures, at least one hole 320 is comprised in the first portion 302 of the delivery cone 30.

As can be seen in FIG. 4, the delivery cone 30 confines within it the cone formed by the aerosol spray 180, without interfering with it.

As a person skilled in the art will readily understand, the proportions and the dimensions of the cone of the aerosol spray 180 depend on certain design variables. In particular, the main variables are the delivery pressure generated by the pump 24, the aperture angle $\gamma$ of the spray 180, which depends on the shape of the nozzle 28, the rheological characteristics and surface tension of the sprayed preparation 18.

Once these parameters are fixed, using certain laboratory tests it is possible to define the shape of the aerosol spray 180. Based on this shape, it is then possible to define the shape of the delivery cone 30. In particular, the shape of the delivery cone 30 makes it possible at the time same to contain the aerosol spray 180 completely without interfering with this and to delimit the portion of the patient's skin that will be reached by the delivery of the preparation.

As can be seen from FIG. 4, the particular shape of the delivery cone 30 with double taper means that in the proximity of the nozzle 28 it diverges from the spray 180, to approach it again in the proximity of the contact rim 300. As a person skilled in the art will note, the at least one through-hole 320 is positioned exactly in the zone in which the delivery cone 30 diverges from the aerosol spray 180.

This positioning of the holes 320 allows the air displaced during delivery of the preparation 18 to exit from the closed space formed by the delivery cone 30 and the patient's skin. The immediate release of the air avoids creating turbulence in the flow of aerosol spray, which remains laminar in the path from the nozzle 28 to the surface of the skin. In this way the amount of preparation 18 that strikes the inside surface of the cone in the proximity of the contact rim 300 is minimized: virtually the total amount of preparation 18 supplied by the pump reaches the surface of the skin, thus guaranteeing standardization of the dose supplied. At the same time, owing to the positioning of the holes 320 and the high delivery pressure from the nozzle 28, only air escapes from the holes 320, and not the fine mist.

As a person skilled in the art will readily understand from the above account, the dispenser 20 according to the present invention achieves the aim of at least partially overcoming the drawbacks highlighted with reference to the prior art. In particular, the dispenser 20 according to the present invention allows precise control of the amount of preparation supplied.

More particularly, the dispenser 20 according to the present invention makes it possible to avoid dispersion of the fine mist and, at the time same, maintain the desired uniformity of administration of the preparation 18.

As described above, the delivery axis X of the nozzle 28 and the axis X' of the delivery cone 30 may coincide on one axis as described, which may otherwise be referred to as single axis X. The single axis X is shown in the drawings. However, the axis X' of the delivery cone 30 may not coincide with the delivery axis X as described above. For example, the axis X' of the delivery cone 30 may be substantially parallel to the delivery axis X. Alternatively, the axis X' of the delivery cone 30 may be at an angle to the delivery axis X and may not coincide with the delivery axis X. There may be an angle θ between the delivery axis X and the axis X' of the delivery cone 30. The angle θ may be greater than 0°, and may be greater than 0° and less than or equal to 200, and preferably less than or equal to 100, and more preferably less than or equal to 5°.

For the purpose of meeting specific requirements, a person skilled in the art will be able to make changes and/or substitutions of elements described with equivalent elements in the embodiments of the dispenser 20 described above, while remaining within the scope of the appended claims.

What is claimed is:

1. Dispenser (20) for spray delivery of a preparation (18), comprising:
   a reservoir (22) suitable for housing the preparation (18);
   a pump (24);
   a load chamber (26);
   a nozzle (28) having a delivery axis (X);
   a delivery cone (30) having an axis (X'); wherein the pump (24) is suitable, at each operation:
   for drawing a predetermined quantity of preparation (18) from the reservoir (22), for supplying such quantity of preparation (18) to the load chamber (26) upstream of the nozzle (28), and
   for creating a delivery pressure in the load chamber (26), and wherein the nozzle (28) is suitable for delivering said quantity of preparation (18) in the form of an aerosol spray (180),
   wherein the delivery cone (30) comprises a contact rim (300) and, in the proximity of the nozzle (28), at least one through hole (320) suitable for putting into communication an inside of the delivery cone (30) with a surrounding environment, characterized in that the at least one through hole (320) is positioned entirely downstream of the nozzle and within the first 20% of a distance/as measured from the nozzle (28) to the contact rim (300); wherein the dispenser (20) is configured so that when the contact rim (300) of the delivery cone (30) is positioned on a patient's skin such that there is a closed space formed by the delivery cone (30), air within the closed space is arranged to flow out of the at least one through hole (320) in response to the spray delivery of the preparation.

2. Dispenser (20) according to claim 1, wherein the delivery cone (30) further comprises a first portion (302) and a second portion (304) having different taper ratios from one another.

3. Dispenser (20) according to claim 2, wherein a generatrix of a surface of the first portion (302) forms with axis (X') an angle α and a generatrix of a surface of the second portion (304) forms with axis (X') an angle β, wherein angle β is smaller than angle α.

4. Dispenser (20) according to claim 2, wherein a generatrix of a surface of the first portion (302) forms with axis (X') an angle α comprised between 40° and 50°.

5. Dispenser (20) according to claim 2, wherein a generatrix of a surface of the second portion (304) forms with axis (X') an angle β comprised between 6° and 16°.

6. Dispenser (20) according to claim 2, wherein in a cross-section lengthways through the delivery cone (30) along the axis (X') of the delivery cone (30), a surface of the first portion is at an angle α to the axis (X') of the delivery cone (30), and a surface of the second portion is at an angle β to the axis (X') of the delivery cone (30), wherein angle β is smaller than angle α.

7. Dispenser (20) according to claim 2, wherein in a cross-section lengthways through the delivery cone (30) along the axis (X') of the delivery cone (30), a surface of the first portion is at an angle α to the axis (X') of the delivery cone (30) and is between 40° and 50°.

8. Dispenser (20) according to claim 2, wherein in a cross-section lengthways through the delivery cone (30) along the axis (X') of the delivery cone (30), a surface of the second portion is at an angle β to the axis (X') of the delivery cone (30), wherein angle β is between 6° and 16°.

9. Dispenser (20) according to claim 2, wherein the first portion (302) extends up to 15%-25% of the distance/ between the nozzle (28) and the contact rim (300).

10. Dispenser (20) according to claim 2, wherein the at least one through hole (320) is comprised in the first portion (302) of the delivery cone (30).

11. Dispenser (20) according to claim 1, wherein the delivery cone (30) comprises a plurality of through holes (320).

12. Dispenser (20) according to claim 1, wherein the delivery axis of the nozzle and the axis of the delivery cone coincide in one single axis (X), even during operation of the dispenser (20).

13. A method of dispensing a volume of fluid onto a skin surface comprising:

a. positioning on the skin surface a contact rim (300), said contact rim defined with a dispenser comprising:
a reservoir (22) suitable for housing a preparation (18);
a pump (24);
a load chamber (26);
a nozzle (28) having a delivery axis (X);
a delivery cone (30) having an axis (X'); wherein the pump (24) is suitable at each operation:
for drawing a predetermined quantity of preparation (18) from the reservoir (22) for supplying such quantity of preparation (18) to the load chamber (26) upstream of the nozzle (28), and
for creating a delivery pressure in the load chamber (26), and wherein the nozzle (28) is suitable for delivering said quantity of preparation (18) in the form of an aerosol spray (180),
wherein the delivery cone (30) comprises the contact rim (300) and, in the proximity of the nozzle (28), at least one through hole (320) suitable for putting into communication an inside of the delivery cone (30) with a surrounding environment, characterized in that the at least one through hole (320) is positioned entirely downstream of the nozzle and within the first 20% of a distance/as measured from the nozzle (28) to the contact rim (300); and
b. dispensing the preparation from the dispenser, wherein the dispenser (20) is configured so that when the contact rim (300) of the delivery cone (30) is positioned on a patient's skin such that there is a closed space formed by the delivery cone (30), air within the closed space is arranged to flow out of the at least one through hole (320) in response to the spray delivery of the preparation.

14. Dispenser (20) for spray delivery of a preparation (18), comprising:
a reservoir (22) suitable for housing the preparation (18);
a pump (24);
a load chamber (26);
a nozzle (28) having a delivery axis (X);
a delivery cone (30) having an axis (X'); wherein the pump (24) is suitable, at each operation:
for drawing a predetermined quantity of preparation (18) from the reservoir (22), for supplying such quantity of preparation (18) to the load chamber (26) upstream of the nozzle (28), and
for creating a delivery pressure in the load chamber (26), and wherein the nozzle (28) is suitable for delivering said quantity of preparation (18) in the form of an aerosol spray (180),
wherein the delivery cone (30) comprises a contact rim (300) and, in the proximity of the nozzle (28), at least one through hole (320) suitable for putting into communication an inside of the delivery cone (30) with a surrounding environment, characterized in that the at least one through hole (320) is positioned entirely downstream of the nozzle and within the first 20% of a distance/as measured from the nozzle (28) to the contact rim (300).

* * * * *